United States Patent [19]

Evers

[11] Patent Number: 4,900,936
[45] Date of Patent: Feb. 13, 1990

[54] DOSIMETER CONSTRUCTION

[75] Inventor: Wolfgang Evers, Lübeck, Fed. Rep. of Germany

[73] Assignee: Drägerwerk Aktiengesellschaft, Lübeck, Fed. Rep. of Germany

[21] Appl. No.: 205,063

[22] Filed: Jun. 10, 1988

[51] Int. Cl.$^4$ .............................................. G01N 33/52
[52] U.S. Cl. ................... 250/474.1; 422/58; 422/86; 436/902
[58] Field of Search ............... 250/472.1, 473.1, 474.1, 250/482.1; 436/902; 422/86, 56, 57, 58

[56] References Cited

U.S. PATENT DOCUMENTS

| | | | |
|---|---|---|---|
| 3,152,253 | 10/1964 | Marchant | 250/474.1 |
| 3,878,108 | 4/1975 | Burgkhardt et al. | 250/472.1 |
| 4,040,805 | 8/1977 | Nelms et al. | 73/23 |
| 4,267,023 | 5/1981 | Frant et al. | 73/23 |
| 4,327,575 | 5/1982 | Locker | 73/23 |
| 4,381,454 | 4/1983 | Griffith et al. | 250/473.1 |
| 4,478,792 | 10/1984 | McConnaughey et al. | 422/56 |
| 4,525,704 | 6/1985 | Campbell et al. | 340/632 |
| 4,680,165 | 7/1987 | Vo-Dinh | 436/91 |
| 4,772,560 | 9/1988 | Attar | 422/56 |

Primary Examiner—Constantine Hannaher
Attorney, Agent, or Firm—McGlew & Tuttle

[57] ABSTRACT

A dosimeter for detection of noxious substances which are collected on a plaque-like substrate carrier, which is closed off against the outside by a diffusion membrane fitted to it, is improved so that a uniform fit can be achieved over the entire surface of the membrane. For this, the substrate carrier is curved outwardly.

5 Claims, 1 Drawing Sheet

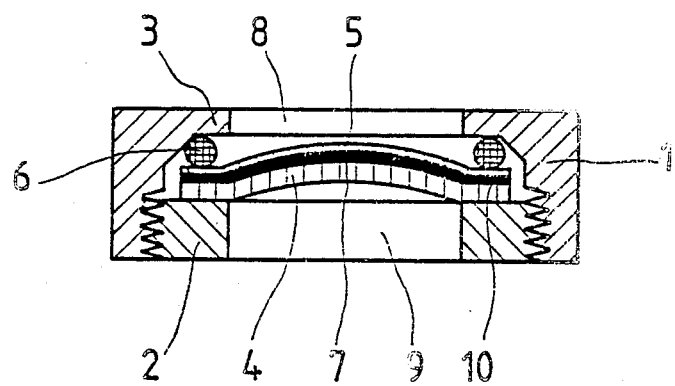

DOSIMETER CONSTRUCTION

FIELD AND BACKGROUND OF THE INVENTION

The invention relates in general to detection devices and in particular to a new and useful dosimeter for detection of noxious substances which are collected on a plaque-like substrate carrier, which is closed off against the outside by a diffusion membrane fitted to it.

A similar dosimeter is known from German OS 27 36 975, whereby a particulate adsorption material for collection of the noxious matter to be detected is filled in a recess housing. This plaque-like substrate carrier is covered by a membrane, which is permeable to the vapors being detected, which then penetrate into the adsorption material and can be detected by a subsequent assay method, such as the wet chemical method.

If such plaques are used with a colorimetric indicator, instead of the familiar adsorption material, it is important that the permeable membrane placed above the substrate carrier has a uniform distance over its entire region of coverage or fit closely on the substrate carrier in constant contact. Different distances also result in different diffusion path lengths, producing different color hues which, in actuality, do not originate in different concentrations of the substance being detected. Therefore, in covering the dosimeter, it is necessary to take the utmost care so that the membranes are uniformly tight and arranged at constant distance from the substrate carrier, which cannot always be achieved when the membranes have small dimensions and sensitivity. Even so, a careful covering may produce folds in the membrane. Fixation of the membrane at its margin produces the largest pressure on the substrate carrier in this place, which falls off steadily toward the center of the membrane and thus produces a pressure gradient, which leads to a varying pressure force on the substrate carrier over the entire stretch of the membrane. This also results in a varying diffusion behavior of the gas being detected from the outside into the substrate carrier, apart from the fact that the excessive fitting pressure and stretching of the membrane produces a locally varying diffusion behavior of the gas within the membrane.

SUMMARY OF THE INVENTION

Thus, the present invention improves a dosimeter in such a way that a uniform arrangement can be achieved over the entire surface of placement of the membrane on the substrate carrier.

The solution is to form the substrate carrier curving toward the outside.

The advantages achieved by the invention includes the fact that the membrane can now be stretched over the curve and no hollows or different distances from the substrate carrier can result. The fitting pressure of the membrane now no longer need be produced, as in the level configuration of the substrate carrier, by an excessive tension at the margin of the membrane, but instead it is naturally produced in moderate form by the placement of the membrane on the curve of the substrate carrier.

It is expedient to fix the membrane only at its margin in the housing of the dosimeter, so that it hugs the shape of the curve.

An especially advantageous configuration is provided when the substrate carrier is represented by a base or margin, which is subjected to an internal stress (compression), while the membrane is placed over the substrate carrier and secured at its margin.

Then, the curving shape is produced by a pressure on the underside of the substrate carrier, so that the formerly loosely lying membrane is placed under a uniform tension, whereby the membrane is fitted evenly to the substrate carrier without folding over the entire region of its surface.

Accordingly, it is an object of the invention to provide an improved dosimeter or device for detection of noxious substances such as gases, comprising a block-like substrate carrier with a diffusion membrane mounted on said carrier and closed off against the outside and wherein the substrate carrier is curved outwardly.

A further object of the invention is to provide a dosimeter which is simple in design, rugged in construction and economical to manufacture.

The various features of novelty which characterize the invention are pointed out with particularity in the claims annexed to and forming a part of this disclosure. For a better understanding of the invention, its operating advantages and specific objects obtained by its uses, reference is made to the accompanying drawings and descriptive matter in which preferred embodiments of the invention are illustrated.

BRIEF DESCRIPTION OF THE DRAWINGS

In the drawings:

The only figure of the drawings is a schematic diagram shown in accordance with the invention.

DESCRIPTION OF THE PREFERRED EMBODIMENTS

Referring to the drawings in particular the invention embodied therein comprises a dosimeter which includes a support carrier ring 2 on which is positioned a substrate carrier 4 having a diffusion membrane 5 on its exterior and being curved outwardly in accordance with the invention.

The single figure shows a dosimeter in section view, which comprises the housing 1, in which a carrier ring 2 is secured by screwing. Between the collar 3 of the housing 1 are secured the substrate carrier 4 and the diffusion membrane 5 at its margin 10 by means of an O-ring 6. On the substrate carrier 4 there is a colorimetric indicator layer 7 sensitive to the noxious substance being detected. The housing has an inlet opening 8 to the outside, from which the substance being detected gets into the diffusion membrane 5 and onto the indicator layer 7. The bottom side of the substrate carrier 4 is accessible through an opening 9 of the carrier ring. From this side, the substrate carrier 4 originally subjected to an internal stress can be converted to the curved shape depicted by exerting a pressure on its underside.

The substrate carrier 4 includes the margin 10, which is secured above the carrier ring 2. However, the substrate carrier 4 can also be integrated with the carrie ring 2 as a single piece. Furthermore, the opening 9 of the carrier ring can be eliminated if the curved shape of the substrate carrier is built in from the outset.

While specific embodiments of the invention have been shown and described in detail to illustrate the application of the principles of the invention, it will be understood that the invention may be embodied otherwise without departing from such principles.

What is claimed is:

1. A dosimeter for detection of noxious substances, comprising: a substrate collection carrier on which the substance is collected, said substrate collection carrier having a top surface; a diffusion membrane overlying said carrier and closing it off against the outside, said substrate carrier being curved outwardly, said diffusion membrane abutting said top surface and hugging the shape of the curve.

2. A dosimeter according to claim 1, wherein said substrate carrier has a flat marginal rim, said diffusion membrane being fixed at said rim over said carrier.

3. A dosimeter according to claim 1, further comprising: a housing defining a chamber with an inlet opening and a carrier ring opening, an O-ring being positionable in said chamber adjacent said inlet opening, each of said substrate collection carrier and said abutting diffusion membrane being insertable in said chamber, a carrier ring fixing said substrate collection carrier and said abutting diffusion membrane within said chamber between said O-ring and said carrier ring.

4. A dosimeter for detection of noxious substances including a substrate collection carrier on which the substrate is collected and a diffusion membrane, formed by the steps of: subjecting the substrate collection carrier to compressive stress; placing the membrane over the substrate carrier; securing the membrane and the substrate carrier about a marginal region; and, applying pressure to a side of the substrate carrier opposite to the overlayed membrane to form a curved shape thereby placing the membrane under a uniform tension to uniformly fit the membrane over the substrate carrier without creating folding areas or buckling areas.

5. A dosimeter for detecting of noxious substances comprising: a housing having a first housing part and a second housing part said first and second housing parts cooperating to define a chamber, said first housing part having an inlet opening; a substrate carrier; a colorimetric indicator layer positioned over said substrate carrier; a gas permeable diffusion membrane positioned over said colormetric indicator layer, each of said substrate layer, diffusion membrane and colorimetric indicator layer being positioned within said chamber and having a marginal area positioned between said first housing portion and said second housing portion, said substrate carrier being curved in a direction of said inlet opening such that said gas permeable membrane abuts said colorimetric indicator layer which abuts said substrate carrier such that said diffusion membrane hugs the shape of the curved substrate carrier.

* * * * *